(12) United States Patent
List

(10) Patent No.: US 6,858,015 B2
(45) Date of Patent: Feb. 22, 2005

(54) BLOOD WITHDRAWAL SYSTEM

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/138,869

(22) Filed: May 3, 2002

(65) Prior Publication Data

US 2003/0028126 A1 Feb. 6, 2003

(30) Foreign Application Priority Data

May 5, 2001 (DE) .......................................... 101 21 883

(51) Int. Cl.[7] .............................................. A61B 5/00
(52) U.S. Cl. ...................................................... 600/583
(58) Field of Search ................................ 600/573, 576, 600/578, 583, 584, 316, 368; 604/157; 606/182

(56) References Cited

U.S. PATENT DOCUMENTS

| 4,924,879 | A |   | 5/1990 | O'Brien |
|---|---|---|---|---|
| 5,029,583 | A | * | 7/1991 | Meserol et al. ............. 600/316 |
| 5,196,025 | A |   | 3/1993 | Ranalletta et al. |
| 5,318,583 | A |   | 6/1994 | Rabenau et al. |
| 5,318,584 | A |   | 6/1994 | Lange et al. |
| RE35,803 | E |   | 5/1998 | Lango et al. |
| 5,997,561 | A |   | 12/1999 | Bocker et al. |
| 6,071,249 | A |   | 6/2000 | Cunningham et al. |

FOREIGN PATENT DOCUMENTS

| EP | 458451 | 11/1995 |
|---|---|---|
| EP | 1034740 | 9/2000 |
| EP | 1090584 | 4/2001 |

* cited by examiner

Primary Examiner—Max F. Hindenburg
Assistant Examiner—Brian Szmal
(74) Attorney, Agent, or Firm—Woodard, Emhardt, Moriarty, McNett & Henry LLP

(57) ABSTRACT

Blood withdrawal system for withdrawing blood for diagnostic purposes, comprising a housing with an outlet opening for the tip of a lancet, a lancet guide and a lancet drive. The lancet drive comprises a plural lever coupling mechanism, forming a connection between the drive element and the lancet during the puncturing movement and comprising two levers connected to each other via a first swivel joint, wherein one of the levers is coupled to the lancet with its end facing towards the lancet by means of a second swivel joint, and the second lever comprises a third swivel joint at the end facing away from the lancet. During the cocking movement, the freedom of movement of the lancet is limited in such a manner that the lancet tip does not protrude from the outlet opening.

9 Claims, 4 Drawing Sheets

Fig. 1
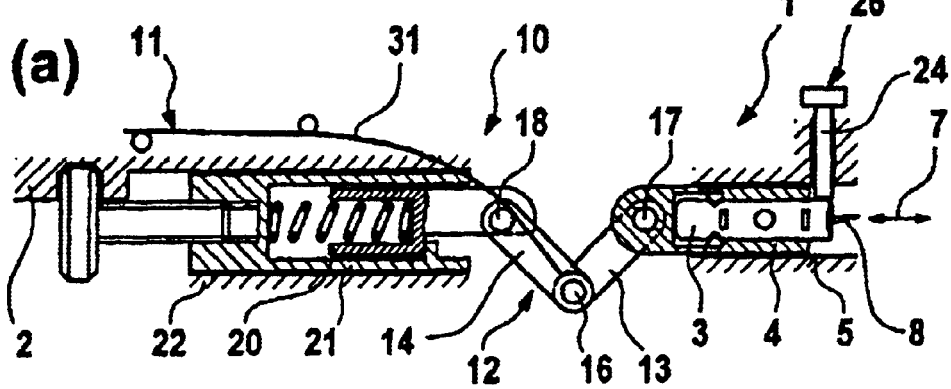
(a)
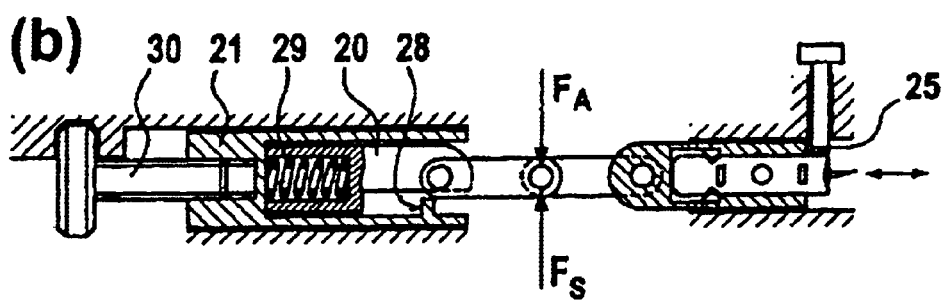
(b)
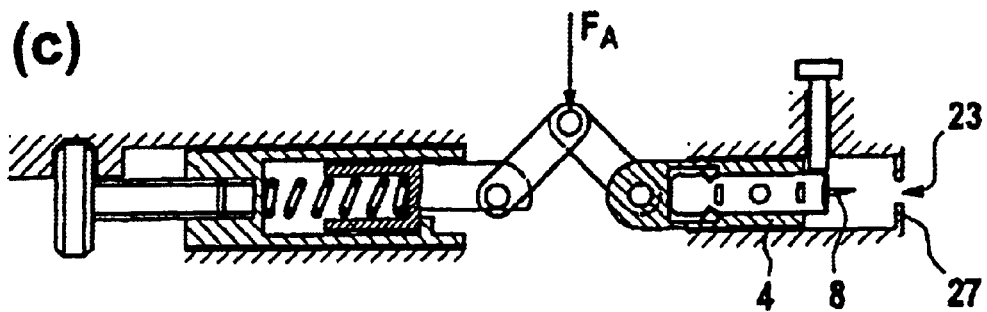
(c)
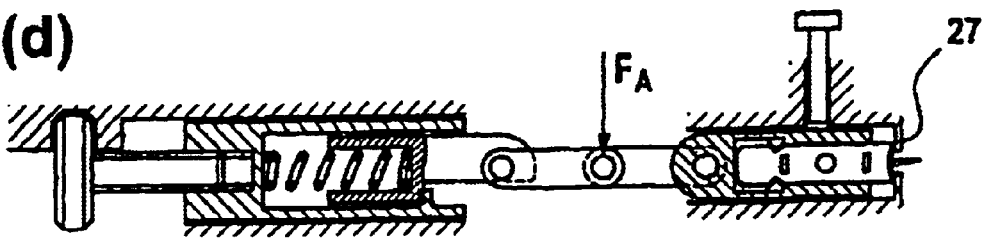
(d)

Fig. 6
(a) 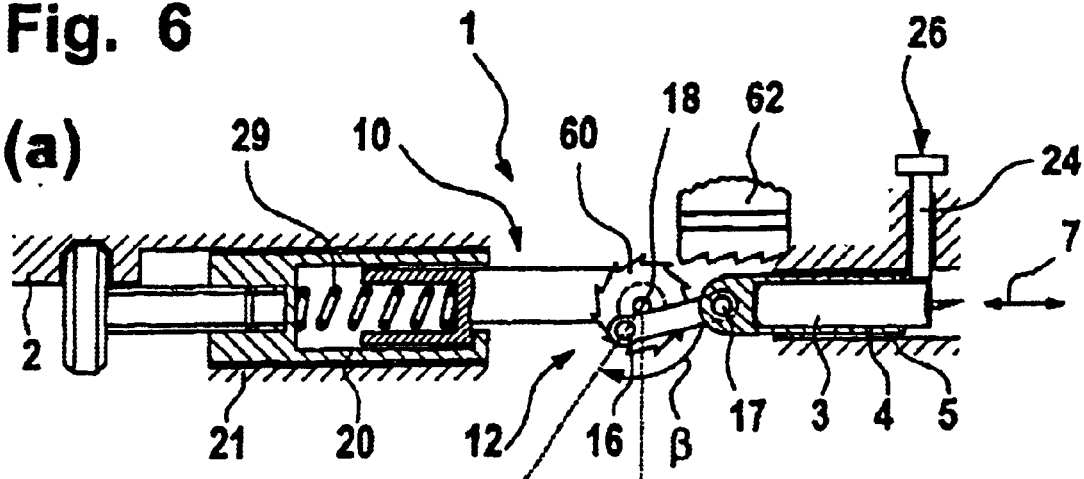
(b) 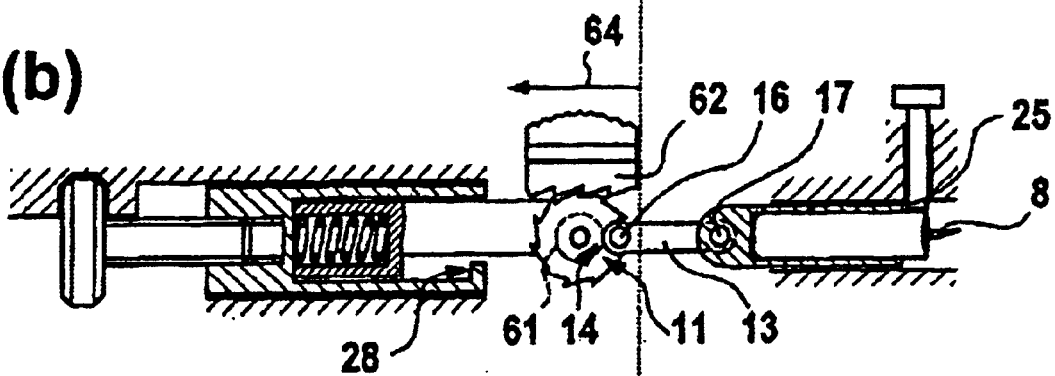
(c) 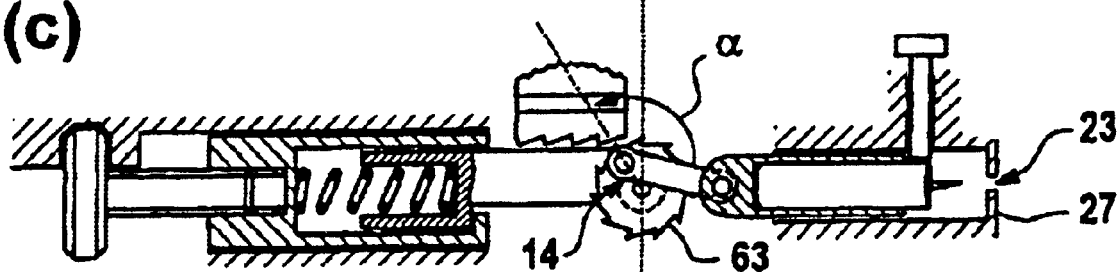
(d) 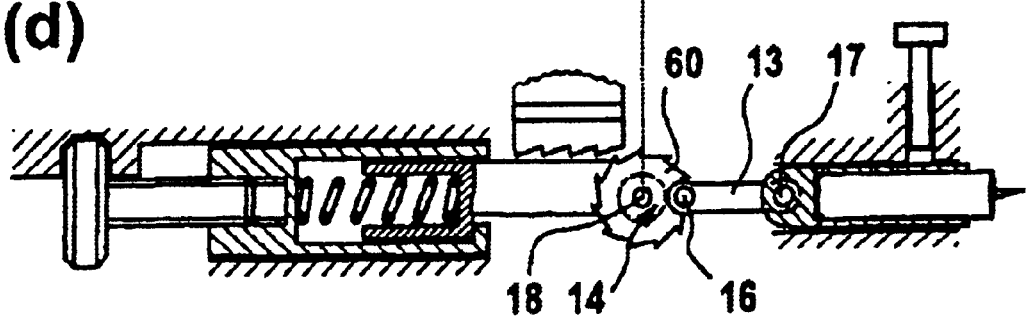

BLOOD WITHDRAWAL SYSTEM

RELATED APPLICATION

This application claims the benefit of German patent application no. 101 21 883.4, filed May 5, 2001.

BACKGROUND

In order to withdraw a small amount of blood from a body part (usually the finger or the earlobe) for analytic-diagnostic purposes, lancets are used which are punctured into the corresponding body part. If the lancets are punctured manually into the skin in order to generate a wound, specially trained staff is necessary. In any case, the puncturing procedure generates considerable pain.

For a long time already, blood withdrawal systems are used which consist of a puncturing device and associated lancets, adapted to the corresponding device. A housing of the puncturing device contains a lancet drive for mechanically driving the lancet into the skin. Normally a spring is used as drive element for the puncturing movement. In an early development phase very simple designs were used, wherein the lancet was fixed directly to the end of a pressure spring located in a housing of longitudinal shape (e.g. U.S. Pat. No. 4,469,110).

Such blood withdrawal systems, however, did not meet the high requirements to be fulfilled if a regular monitoring of certain analytical blood values is necessary. This is particularly true for diabetics who must control their blood glucose level frequently in order to maintain it continuously within certain target limits, by the adaptation of insulin injections with respect to the demand (which varies strongly depending on food intake and physical activities). Extensive scientific investigation proved that an intensive therapy with at least four blood analyses per day results in a dramatic decrease of the most severe late damages of Diabetes Mellitus (for example, a retinopathy with subsequent ablepsia of the patient).

However, such an intensive therapy requires a blood withdrawal with as little pain as possible. Several blood withdrawal systems were developed with the objective to achieve an improvement in this respect. Examples for this development are described in the subsequently discussed publications.

The design described in U.S. Pat. No. 4,924,879 features a spiral driving spring acting upon a rotor the rotation of which is converted, by means of a connecting rod, to a puncturing and retraction movement of the lancet. The pain is supposed to be decreased by the high speed of this movement. However, this design requires precisely machined metal parts and is expensive and relatively bulky. Another disadvantage of this design is the fact that during cocking of the lancet drive the lancet protrudes from the outlet opening, thus resulting in danger of injury.

U.S. Pat. No. 4,924,879 describes a design wherein the necessary connection between a drive element (realized as a leaf spring or a spiral spring) and the lancet is formed by two levers connected to each other by means of a swivel joint. One of the levers is connected, with its end facing the lancet, to the lancet by means of a second swivel joint, whereas the other lever is connected to the housing by means of a third swivel joint. The swivel axes of all three swivel joints are parallel to each other. In the cocked state, the toggle joint formed by the two levers is in a first bent position. After actuating a release button, it is moved by the force of the drive spring via a straight position to a second bent position, in which the first swivel joint is located, with respect to the initial position, on the other side of a plane defined by the puncture path of the lancet and the axis of the second swivel joint. In this design, too, the lancet protrudes from the outlet opening during the cocking process.

Blood withdrawal systems with the lancet drive described in U.S. Pat. No. 5,318,584 are used extensively. The users in particular appreciate the unsurpassed low level of pain. The core element of this drive is a rotor the rotor axis of which coincides with the longitudinal axis of the oblong (pencil-shaped) device. This rotor is driven by a coaxial spiral spring. Its rotational movement is converted to the required translational movement of the lancet by means of a cam control. The design of the cam control allows to cock the device without protrusion of the lancet tip from the housing. The rotation of the rotor around the longitudinal axis of the device minimies vibrations and stabilizes the puncturing process. However, the design consists of many parts with complicated shapes and therefore it is rather expensive. A newer version of a blood withdrawal system with a rotor rotating around the longitudinal axis is described in EP 1034740 A1.

In EP 1090584 A2 a further design of the rotor principle is described which reduces the constructive expense by using a drive rotor with a special shape, wherein the rotation of the rotor is caused by the force of the drive spring pressing against a correspondingly shaped pressure surface of the drive rotor. In this case too, the movement of the drive rotor is converted into a corresponding movement of the lancet by means of a cam control. This design requires a relatively wide housing form which is considered unfavorable by many users.

SUMMARY

In spite of the extensive development work resulting in the designs mentioned and several further designs, there is substantial interest in a blood withdrawal system which complies with all the following requirements, which are partially contradictory:

minimum pain sensation, operation as simple as possible, compact, sleek shape and simple, cost effective construction.

A substantial progress in this respect is obtained with the blood withdrawal system according to the invention which comprises a housing with an outlet opening for the tip of a lancet which is moveable in the housing along a predetermined puncture path, a lancet guide, guiding the lancet on the predetermined puncture path, and a lancet drive, converting a movement of a drive element, after the actuation of a trigger, into the puncturing movement in which the lancet is moved with high speed along the predetermined puncture path in the puncturing direction, until its tip protrudes from the outlet opening. The lancet drive comprises a plural lever coupling mechanism forming a connection between the drive element and the lancet during the puncturing movement and comprising two levers connected to each other by means of a first swivel joint. One of the levers is coupled, at the end directed towards the lancet, to the lancet by means of a second swivel joint. The second lever comprises, at the end directed away from the lancet, a third swivel joint. During the puncturing movement, the plural lever coupling mechanism is moved from a first bent position corresponding to the cocked state of the lancet drive, via a straight position corresponding to the maximum puncturing depth, into a second bent position corresponding to the relaxed state of the lancet drive. During the cocking movement, it is moved from the second bent position via the straight position to the first bent position. The freedom of movement of the lancet during the cocking movement is limited in such a manner that the lancet tip does not protrude from the outlet opening. The third swivel joint is fixed to a moveable bearing part which during the cocking process moves in the housing in opposite direction to the puncturing direction. The freedom of movement of the bearing part is during the puncturing movement limited in the direction opposite to the puncturing direction.

Contrary to the described recent development, the invention refers back to the design described in EP 0458451 A1, in which the connection between the drive spring (or another appropriate drive element) and the lancet is formed by two levers, which are connected to one another and to the lancet by swivel joints (similar to a toggle joint)

In the scope of the present invention, the term "lever" designates a constructive element which is rigid and which forms a connection between two force application points each of which is a swivel joint. The design shown in EP 0458451 A1, in which the levers are shaped as rods extending between the swivel axes, is only one of several possibilities. Other shapes are also possible for the realization of the lever components, as will be explained later.

According to the invention, the lancet and the bearing part, to which the rear end of the coupling mechanism is linked, are subject to different movement restrictions during the different movement phases.

During the cocking phase, the lancet is limited, preferably by means of the trigger which is anyhow required, in puncturing direction in such a manner that its tip cannot protrude from the outlet opening of the housing. Thus, the danger of injury is avoided. On the other hand, the bearing part to which the third swivel joint is fixed is moveable towards the rear (i.e., against the puncturing direction) and thereby allows the increase in length of the coupling mechanism which is necessary during cocking.

During the puncturing phase the lancet is free to perform the puncturing movement. However, the freedom of movement of the bearing part towards the rear is limited at least as far as necessary to ensure the required protrusion of the lancet tip from the outlet opening during the puncturing movement.

The practical evaluation of the invention has shown that this combination of measures allows to use a plural lever coupling mechanism—so far only in practical use for simple disposable systems—in a high quality product having very positive characteristics with respect to the previously explained requirements.

BRIEF DESCRIPTION OF THE DRAWINGS

The invention is hereafter described in more detail by reference to the embodiments shown in the figures. The features described can be used individually or in any combination to create preferred embodiments of the invention.

In the figures

FIG. 1 shows a longitudinal section of a highly schematic representation of a blood withdrawal system according to the invention in four different moving positions (a) to (d) of the lancet drive, FIG. 6 shows a representation analogous to FIG. 1 of an alternative embodiment of the lancet drive.

DESCRIPTION

Figure 2:
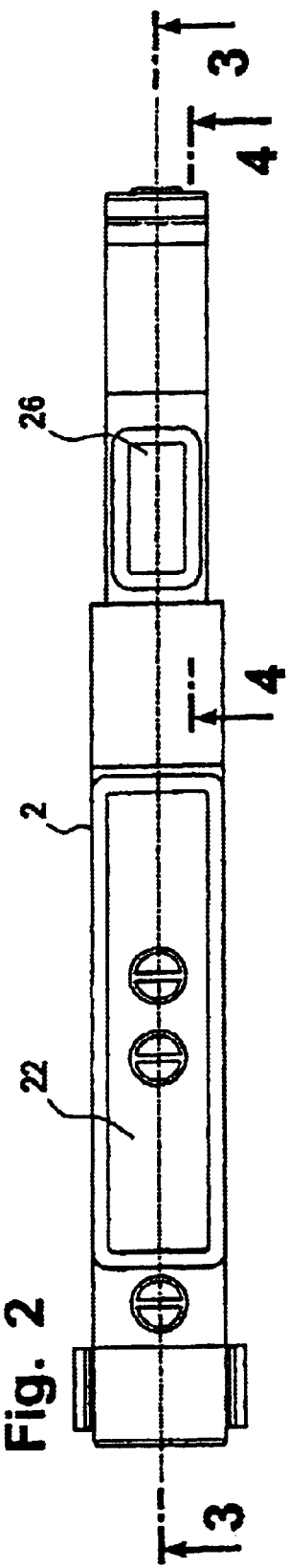
FIG. 2 shows a top view onto the puncturing device of a blood withdrawal system used for the experimental evaluation of the invention.

The blood withdrawal system 1 comprises a puncturing device 2 (only partially shown in FIGS. 1 and 5) and lancets 3. In the shown embodiments, the lancet 3 is exchangably fixed in a lancet holder 4. The lancet holder 4 is guided by a lancet guide 5 during the puncturing movement of the lancet on a predetermined puncture path 7. Thus, the guiding of the lancet 3 on the puncture path 7 is achieved indirectly via the lancet holder 4. The invention is, however, also usable with "directly guided" lancets which are during the puncturing movement coupled to the lancet drive of the puncturing device only with the end opposed to the lancet tip 8, and guided directly (in particular by the surrounding housing wall).

During the puncturing and retraction movement, the lancet 3 is coupled (in the shown embodiment indirectly via the lancet holder 4) to a lancet drive 10, which essentially consists of a drive element 11 and a power transmission coupling mechanism, in the case of the invention a plural lever coupling mechanism 12. In the embodiments shown in FIGS. 1 to 4, the plural lever coupling mechanism 12 has two levers, namely a lancet side lever 13 and a drive side lever 14, swivelably connected to each other by a first swivel joint 16 (similar to a toggle joint). At its end facing the lancet 3, the lancet side lever 13 is coupled to the lancet 3, via a second swivel joint 17 and via the lancet holder 4. At its end facing away from the lancet 3, the drive side lever 14 is connected to a bearing part 20. The bearing part 20 is seated moveably in the housing 22 of the puncturing device 2 by means of a bearing part guide 21, in such a manner that it is able to perform a movement against the puncturing direction (i.e. a movement which has at least a component directed against the puncturing direction). The swivel axes of the swivel joints 16 to 18 run parallel to each other and perpendicular to the drawing plane of the figures.

In the embodiment shown in FIG. 1, the necessary limitation of the freedom of movement of the lancet 3 is achieved by a locking bolt 24 which is movable in a direction transversal to the puncturing direction. The end of the locking bolt 24 facing the lancet 3 forms a stop element 25, limiting the movement path of the lancet 3 in puncturing direction (indirectly via the lancet holder 4) during the cocking movement of the lancet drive 10. The locking bolt 24 simultaneously serves as trigger 26 of the lancet drive.

The freedom of movement of the bearing part 20 within the bearing part guide 21 is limited in the puncturing direction (towards the front side) by a stop 28, and elastically limited against the puncturing direction (towards the rear) by a pressure spring 29, which is supported at one end by the bearing part 20 and at the other end by a component 30 fixed (at least against the puncturing direction) to the housing. Preferably, the pressure spring 29 is pretensioned, i.e. it exercises a pressure force even if it is in the position of its maximum expansion (movement positions a, c and d).

The cocking movement phase of the lancet drive 10 starts with a first bent position a and leads via a straight position b into a second bent position c. A cocking force $F_S$ which is stronger than the opposite force $F_A$ of the drive element 11, is exercised, by means of a movement mechanism not shown in FIG. 1, onto the plural lever coupling mechanism 12. The drive element can be formed, for example, by a leaf spring 31 which, for reasons of clearness, is shown only in FIG. 1(a) but, of course, in every movement phase presses with a driving force $F_A$ onto the plural lever coupling mechanism.

During the cocking movement phase, the freedom of movement of the lancet 3 is limited in puncturing direction by a stop 25 of the trigger 26. The movement from a to b has the effect that the bearing part 20 is shifted, against the force of the pressure spring 29, in the direction opposite to the puncturing direction. During the further movement towards c the pressure spring 29 relaxes, and at the end of this movement the lancet drive 10 is in the cocked state (movement position c).

For triggering the puncturing movement, the trigger 26 is pulled out of the movement path of the lancet holder 4, so that the lancet drive, driven by the drive force $F_A$ of the drive element 11, performs a movement from the position c via the position d (maximum puncturing depth) and further to the initial position a. During this movement the tip 8 of the lancet 3 protrudes from an outlet opening 23 (only shown at the movement positions c and d). The outlet opening 23 is surrounded by a contact surface 27 against which the body part from which blood is to be withdrawn is pressed during the use of the device.

During the puncturing movement phase the bearing part 20 should be in a defined position in order to guarantee an exactly reproducible puncturing depth. Therefore, the force of the pressure spring 29 must be dimensioned such that the bearing part 20 is pressed at least in the movement position of the maximum puncturing depth (d in FIG. 1) against the stop 28 limiting its movement in puncturing direction.

Figure 3:
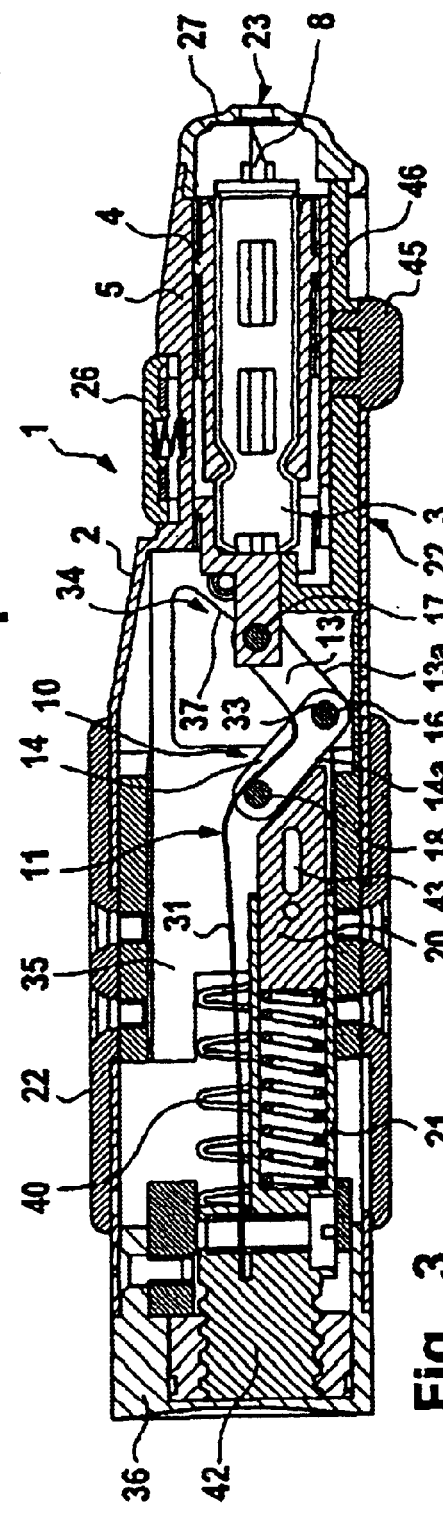
FIG. 3 shows a longitudinal section through the device shown in FIG. 2 along the line A—A.
Figure 4:
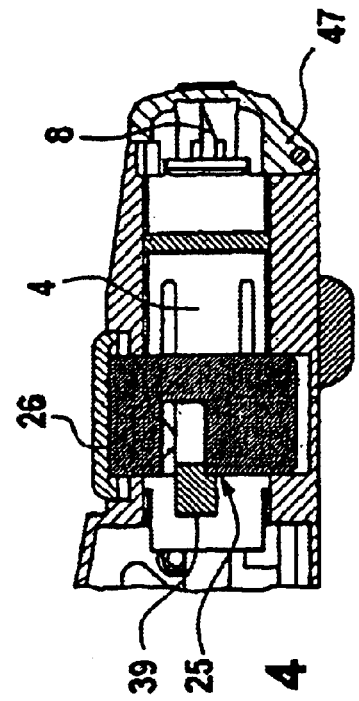
FIG. 4 shows a partial longitudinal section through the device shown in FIG. 2 along the line B—B.

FIGS. 2 to 4 show constructive details of a blood withdrawal system used for the experimental evaluation of the invention. Here the levers 13 and 14 are each formed by two parallel metal rods 13a, 14a. FIG. 3 shows a front rod of each lever, covering the respective rear rod. The swivel joint 16 is formed by a straight bolt 33 sitting in corresponding bores of the rods 13a, 14a and passing through a recess 34 of a cocking slide 35 located between the rods. For cocking, the cocking slide 35 is pushed backwards by means of an actuation button 36, whereby the bolt 33 slides over an inclined surface 37 of the recess 34, thus being moved towards the cocked state (upwards in FIG. 3). As in FIG. 1 a stop element 25 coupled to the trigger 26 meshes in the cocked state (FIG. 4) into a corresponding counterpart 39 of the lancet holder 4, thus limiting the movement of the lancet 3 in puncturing direction in such a manner that the lancet tip 8 during the cocking movement phase of the lancet drive 10 cannot move out of the outlet opening surrounded by the contact surface 27. The cocking slide 35 is pushed back to its initial position by a flat spring 40.

In the embodiment shown, the puncturing depth can be adjusted by turning the actuation button 36. An inner thread of the actuation button 36 cooperates with an outer thread located at the circumference of a slide part 42 which is connected to the bearing part guide 21. A pin, not shown in the figures, is fixed to the bearing part guide 21 and penetrates into a corresponding oblong hole 43 of the bearing part 20, thus limiting the maximum shifting path of the bearing part 20 in puncturing direction and against the puncturing direction. When the actuation button 36 is turned, the shifting of the bearing part guide 21 effects a corresponding shifting of the entire lancet drive 10 and, thus, a change of the puncturing depth.

With the lancet drives known so far, it was not possible to adjust the puncturing depth by shifting the coupling mechanism connecting the drive spring to the lancet or the lancet holder in its entirety, and thus providing the corresponding adjustment mechanism at the end of the puncturing device remote from the outlet opening. In practice, the adjustment of the puncturing depth was only possible by making the position of the front cap of the puncturing device (where the contact surface 27 is located) adjustable in puncturing direction. This causes a concentration of functions in the front part of the puncturing device which leads to difficulties of the construction.

The invention offers the possibility to spatially separate the functions "holding the lancet" and "adjusting the puncturing depth", and to realize these two functions independent from each other. This provides space for additional advantageous functions. For example, the shown embodiment features a slide 45 with an ejector 46 in the area of the lancet holder, serving for ejecting used lancets. The contact surface 27 is a part of a hinged cap 47.

Figure 5:
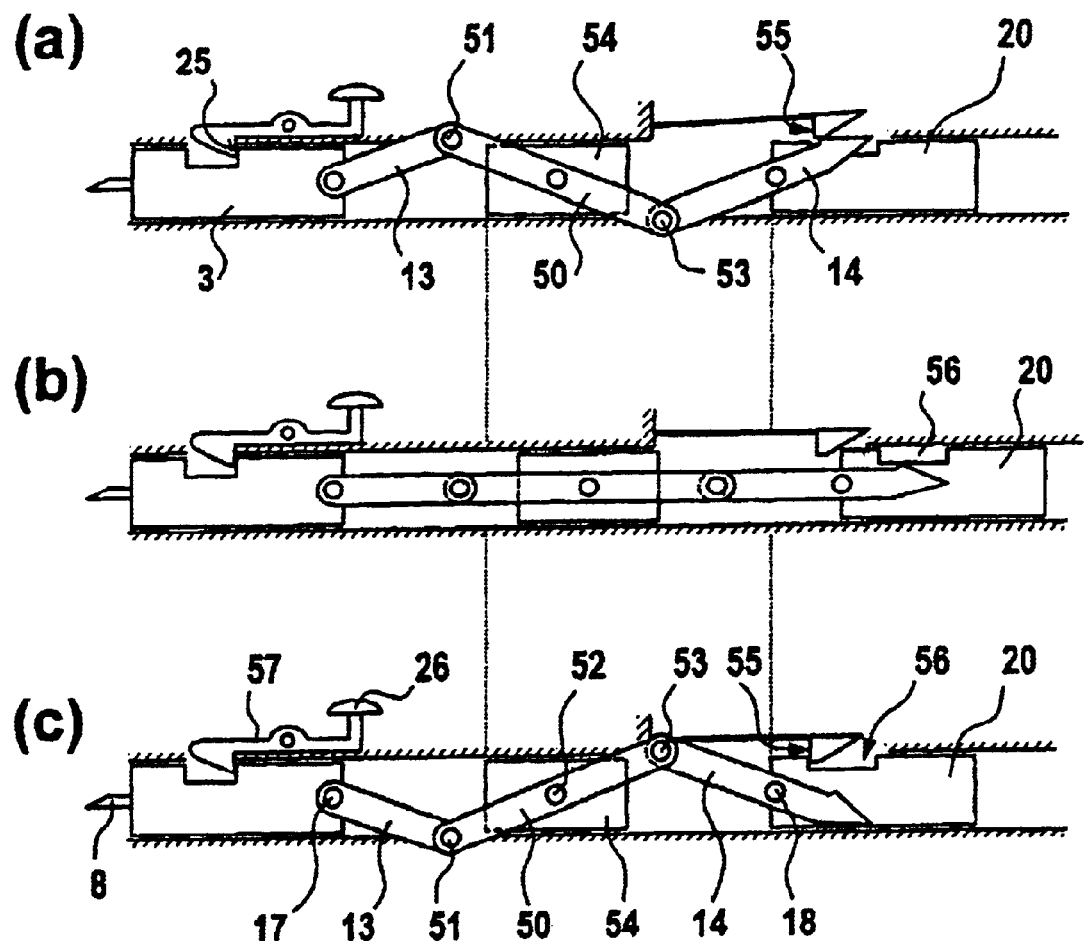
FIG. 5 shows a longitudinal section of a highly schematic representation of an alternative embodiment of a blood withdrawal system according to the invention in three movement positions (a) to (c)

FIG. 5 shows an alternative embodiment which differs from FIGS. 1 to 4 in particular by the fact that the plural lever coupling mechanism 12 comprises three levers, namely a connection lever 50 in addition to the lancet side lever 13 and the drive side lever 14. Five swivel joints are necessary for coupling the levers. Instead of one swivel joint 16 serving for connecting the levers 13 and 14, three swivel joints 51 to 53 are present at the connection lever, the swivel joints 51 and 53 serving for the connection to the levers 13 and 14 and the central swivel joint 52 being fixed to a second moveable bearing part 54 which is during the cocking process moveable against the puncturing direction, just as bearing part 20. For a given length of the puncture path, the deflection of the connecting joints 51 and 53 between the two bent positions (a) and (c) is reduced if more than two levers are used. This allows a sleeker design of the housing.

The movement positions (a) to (c) correspond to the movement positions of FIG. 1 which are designated with the same letters. Therefore, a separate explanation is not necessary. A distinctive design feature is the fact that the limitation of the freedom of movement of the bearing part 20 during the puncturing movement is not provided by an elastically deforming spring, but by means of a stop element 55 which penetrates into a corresponding recess 56 of the bearing part 20 when the lancet drive is in the cocked movement position c. The puncturing phase is triggered by pressing the trigger 26, being connected to the stop element 25 via a catch 57. During cocking, the stop element 25 limits the freedom of movement of the lancet 3 in puncturing direction.

FIG. 6 shows another embodiment of a blood withdrawal system in a presentation analogous to FIG. 1; i.e. the following movement positions are shown as in FIG. 1:
  (a) Lancet drive 10 relaxed; plural lever coupling mechanism 12 in the second bent position;
  (b) Lancet drive 10 during the cocking phase; plural lever coupling mechanism 12 in straight position;
  (c) Lancet drive 10 cocked; plural lever coupling mechanism in the first bent position;
  (d) Lancet drive 10 in the puncturing phase; plural lever coupling mechanism in the straight position corresponding to the maximum puncturing depth.

Corresponding constructive elements are designated with the same reference numerals as in FIG. 1 and are not explained again.

Divergent from FIGS. 1 to 4, the drive side lever 14 of the coupling mechanism 12 is not formed by a rod-shaped constructive element, but by a rotor 60 which is rotatable around the swivel axis 18. The angular separation α of the swivel movement of the second lever 14 formed by the rotor part 60 between the cocked state c and the straight state b, or d, respectively, is more than 90°, in the shown case approximately 135°. The angular separation β between the straight positions b, d and the relaxed position is also more than 90°.

The torque necessary for the swivel movement during the cocking of the lancet drive 10 as well as during the puncturing movement must be provided by means of a constructive element appropriate for such a large swiveling angle. Particularly appropriate for the use as drive element 11 is a torsion spring 61, located behind the rotor part 60 in FIG. 6 and therefore shown in dotted line only in the partial figure b.

A cocking element 62 which is moveable in longitudinal direction, is particularly appropriate for cocking. During its backward movement (i.e. against the puncturing direction) this cocking element 62 is coupled to the drive side lever 14 in such a manner that the torque necessary for cocking is applied to the lever 14 (formed by the rotor part 60). For the shown embodiment this is realized by the fact that the rotor part 60 has a ring gear on its circumference, into which corresponding gear-shaped latches (which are provided at the bottom of the shiftable cocking element 62) mesh when the cocking element 62 is pushed backwards, i.e. in the direction marked with the arrow 64 in partial figure b. Of course, the required freewheeling function can also be provided by other means known for this purpose. The cocking element 62 is moveable in transversal direction against the force of a spring not shown, so that it slides, during the reset, over the ring gear 63, from the position shown in partial figure d into the position according to partial figure a, without turning the rotor 60.

This embodiment shows that the levers 13, 14 must not necessarily be formed by rod-shaped elements, but that a rotating part which has the characteristics of a lever in the meaning explained above can also be used. The embodiment of a plural lever coupling mechanism shown in FIG. 6 resembles a crank drive. It is favorable in that a relatively large puncturing depth can be realized with a given maximum width of the drive.

I claim:

1. A blood withdrawal system for diagnostic purposes, comprising
    a housing with an outlet opening for the tip of a lancet, which is movable in the housing along a predetermined puncture path,
    a lancet guide for guiding the lancet on the predetermined puncture path and
    a lancet drive by which a movement of a drive element is converted into a puncturing movement after the actuation of a trigger, whereby the lancet is moved with high speed along the predetermined puncture path in puncturing direction until its tip protrudes from the outlet opening,
wherein
    the lancet drive comprises a plural lever coupling mechanism forming a connection between the drive element and the lancet during the puncturing movement and comprising two levers connected to each other by means of a first swivel joint,
    one of the levers is coupled to the lancet by means of a second swivel joint, and the second lever comprises a third swivel joint at its end facing away from the lancet, and
    the plural lever coupling mechanism is moved, during the puncturing movement, from a first bent position via a straight position corresponding to the maximum puncturing depth to a second bent position, and is moved, during a cocking movement, from the second bent position via the straight position to the first bent position,
    the freedom of movement of the lancet is limited during the cocking movement in such a manner that the lancet tip does not protrude from the outlet opening, and
    the third swivel joint is connected to a moveable bearing part which during the cocking movement moves inside the housing in a direction opposite to the puncturing direction, and the freedom of movement of which is limited during the puncturing movement in the direction opposite to the puncturing direction.

2. A blood withdrawal system according to claim 1, wherein the freedom of movement of the lancet is limited during the cocking movement by means of a trigger for triggering the puncturing movement.

3. A blood withdrawal system according to claim 1, wherein the freedom of movement of the lancet is limited by a stop element.

4. A blood withdrawal system according to claim 1, wherein the freedom of movement of the bearing part is limited during the puncturing movement by a stop element.

5. A blood withdrawal system according to claim 1, wherein the freedom of movement of the bearing part is limited during the puncturing movement elastically by a spring.

6. A blood withdrawal system according to claim 5, wherein the spring is pretensioned.

7. A blood withdrawal system according to claim 1, wherein the plural lever coupling mechanism comprises three levers.

8. A blood withdrawal system according to claim 1, wherein the angular separation of the swivel movement of the second lever between the first bent position and the straight position corresponding to the maximum puncturing depth exceeds 90°.

9. A blood withdrawal system according to claim 8, wherein the drive element is a torsion spring acting on the second lever.

* * * * *